US 6,179,781 B1

(12) United States Patent
Phillips

(10) Patent No.: US 6,179,781 B1
(45) Date of Patent: Jan. 30, 2001

(54) MEDICAL DIAGNOSTIC ULTRASOUND METHOD AND APPARATUS FOR IMPROVING DOPPLER PROCESSING

(75) Inventor: Patrick J. Phillips, Sunnyvale, CA (US)

(73) Assignee: Acuson Corporation, Mountain View, CA (US)

(*) Notice: Under 35 U.S.C. 154(b), the term of this patent shall be extended for 0 days.

(21) Appl. No.: 09/282,800

(22) Filed: Mar. 31, 1999

(51) Int. Cl.$^7$ ............................................. A61B 8/12
(52) U.S. Cl. ............................................. 600/454
(58) Field of Search ........................ 600/440, 441, 600/443, 447, 453, 455, 458

(56) References Cited

U.S. PATENT DOCUMENTS

| | | | |
|---|---|---|---|
| 4,534,357 | * | 8/1985 | Powers ................................ 600/455 |
| 5,035,245 | * | 7/1991 | Nakamura et al. ................. 600/455 |
| 5,046,500 | | 9/1991 | Fehr . | |
| 5,083,567 | * | 1/1992 | Uchibori ............................. 600/455 |
| 5,183,047 | | 2/1993 | Burckhardt . | |
| 5,431,169 | * | 7/1995 | Gondo ................................ 600/455 |
| 5,675,554 | | 10/1997 | Cole et al. . | |
| 5,882,315 | * | 3/1999 | Ji et al. ............................... 600/553 |
| 5,891,038 | * | 4/1999 | Seyed-Bolorforosh et al. ... 600/447 |
| 5,961,460 | * | 10/1999 | Guracar et al. ..................... 600/440 |
| 5,961,462 | * | 10/1999 | Loupas et al. ...................... 600/453 |
| 6,048,316 | * | 4/2000 | Zhao et al. .......................... 600/447 |

OTHER PUBLICATIONS

H. J. Nitzpon et al., *A New Pulsed Wave Doppler Ultrasound System to Measure Blood Velocities Beyond the Nyquist Limit*; Mar., 1995; vol. 42, No. 2, pp. 265–279.

* cited by examiner

Primary Examiner—Marvin M. Lateef
Assistant Examiner—Ali M. Imam
(74) Attorney, Agent, or Firm—Craig A. Summerfield; Brinks Hofer Gilson & Lione

(57) ABSTRACT

A method and system for Doppler processing of information at two or more different frequency bands for improved accuracy is provided. Signals from two or more unique frequency bands are processed separately to detect motion. Using signals at different frequency bands allows for more effective use of unused bandwidth to increase information content and improve estimation accuracy. One of or more of the two or more receive frequency bands may be within the transmitted fundamental frequency band or within harmonic frequency bands of the transmitted fundamental frequency band. The increased information content generated by using two separate narrow receive frequency bands is used to improve many aspects of motion detection. The resulting Doppler values of each parameter, such as velocity, energy, and variance parameters, are averaged or otherwise combined. One of the average, the Doppler values at each frequency band and a null value are selected for further processing and display. The resulting Doppler images may have improved accuracy and precision, without a loss in frame rate, resolution or displayed area. Further, the parameter selection process can be used to further improve differentiation between blood flow and clutter. Signals at two different frequency bands are also used to further improve detection of velocities beyond the conventional alias limit. Energies of one narrow frequency band at higher frequencies is exposed to more significant attenuation than energies of a lower frequency band, contributing to inferior SNR and potentially poor velocity estimates in some cases. Energy estimates are used to identify inferior SNR. Energy estimates are screened to determine application of an algorithm to detect velocities beyond the individual conventional maximum velocity limits for either of the two narrow frequency bands.

79 Claims, 4 Drawing Sheets

$P_i$ = PARAMETERS FOR BAND $i$ PROCESSING
$P_j$ = PARAMETERS FOR BAND $j$ PROCESSING
$P_N$ = NEW PARAMETERS FOR DISPLAY

MEDICAL DIAGNOSTIC ULTRASOUND METHOD AND APPARATUS FOR IMPROVING DOPPLER PROCESSING

BACKGROUND OF THE INVENTION

This invention relates to a medical diagnostic ultrasound system and method for improving Doppler processing, such as color flow imaging. In particular, increasing the accuracy of Doppler estimates is provided by using signals at multiple frequency bands.

Doppler imaging comprises receiving signals in a single frequency band, such as at a fundamental frequency band or at a second harmonic frequency band of the fundamental frequency band. Typically, the frequency band is narrowly defined within the available broadband system bandwidth, increasing the amount of transmitted power and the signal to noise ratio (SNR).

One ensemble of received signals is processed to estimate motion at each point in space along an ultrasound line. This process is repeated over many ultrasound lines within an image frame.

Doppler imaging of tissue and blood is a qualitative diagnostic tool. The tool remains qualitative partly due to the inaccuracies of estimates. The demand for adequate frame rates, diagnostic resolution, and reasonable interrogated areas dictate that an ultrasound system typically only transmit 2 to 16 pulses to insonify any distinct point in space. This constraint may create estimate drop-outs in flow fields and demand extensive spatial and/or temporal averaging of estimates resulting in inaccurate differentiation between flow and tissue.

Some processes to increase sensitivity to Doppler velocities above conventional maximum velocity detection limits use signals at two different frequency bands. Conventional Doppler systems may not provide for accurate detection of velocities beyond a maximum value determined primarily by the center frequency within a single receive band. The sensitivity to velocities above this limit (the aliasing limit) is increased by using two different frequency bands. The difference between Doppler frequencies obtained from two separate narrow frequency bands is calculated. Since this difference Doppler frequency is less than the Doppler frequency from either of the two frequency bands independently, the maximum detect able Doppler frequency is extended.

For example, Powers describes in U.S. Pat. No. 4,534,357 a system that transmits broad, single band, pulses and then processes receive signals from two narrow receive bands for each broadband pulse transmitted. In other examples, Fehr in U.S. Pat. No. 5,046,500 and Burckhardt in U.S. Pat. No. 5,183,047 describe systems that transmit pulses composed of two separate narrow frequency bands and then process signals from a corresponding two narrow receive bands for each transmitted pulse. However, methods extend the maximum detectable velocities only.

In Ultrasound Imaging Enhancement Methods and Systems, by Ismayil Guracar et. al., U.S. application Ser. No. 08/838,920, now U.S. Pat. No. 5,961,460, filed Apr. 11, 1997, imaging enhancements using two different frequency bands are disclosed. In one embodiment, two different types of scan-converted images are combined into a single image by using a two-dimensional look-up-table (LUT). For example, an image of contrast agents corresponding to a harmonic frequency band is combined with an image corresponding to a fundamental frequency band. In one further embodiment in the above referenced application, "either or both of the fundamental and harmonic images are generated from signals detected by the Doppler detector 22 with no clutter filtering" (page 16).

BRIEF SUMMARY

The present invention is defined by the following claims, and nothing in this section should be taken as a limitation on those claims. By way of introduction, the preferred embodiment described below includes a method and system for Doppler processing of information at two different frequency bands.

Signals from two or more unique frequency bands are processed separately to detect motion. The resulting Doppler values of each parameter, such as velocity, energy, and variance parameters, are averaged or otherwise combined. One of the average, the Doppler values at each frequency band and a null value are selected for further processing and display. The resulting Doppler images may have improved accuracy and precision, without a loss in frame rate, resolution or displayed area. Further, the parameter selection process can be used to further improve differentiation between blood flow and clutter.

Using signals at different frequency bands allows for more effective use of unused bandwidth to increase information content and improve estimation accuracy. One of or more of the two or more receive frequency bands may be within the transmitted fundamental frequency band or within harmonic frequency bands of the transmitted fundamental frequency band. The increased information content generated by using two separate narrow receive frequency bands is used to improve many aspects of motion detection, not just the sensitivity to velocities beyond the conventional maximum detectable velocities.

In one embodiment, signals at two different frequency bands are used to further improve detection of velocities beyond the conventional limit. Energies of one narrow frequency band at higher frequencies is exposed to more significant attenuation than energies of a lower frequency band, contributing to inferior SNR and potentially poor velocity estimates in some cases. Energy estimates are used to identify inferior SNR. Energy estimates are screened to determine application of an algorithm to detect velocities beyond the individual conventional maximum velocity limits for either of the two narrow frequency bands.

In a first aspect, a medical diagnostic ultrasound method and system for Doppler processing are provided. First and second receive signals at first and second frequency bands, respectively, are obtained. The first frequency band is different than the second frequency band. First and second Doppler values of a same type of Doppler parameter are determined from the first and second receive signals, respectively. A value is selected from a group consisting of two or more of: the first Doppler value, the second Doppler value and a third Doppler value that is a combination of the first and second Doppler values. A Doppler display responsive to the selected value is generated.

In a second aspect, other medical diagnostic ultrasound systems and methods for Doppler processing are provided. First and second receive signals at first and second frequency bands, respectively, are obtained, where the first frequency band is different than the second frequency band. First and second Doppler values of a same type of Doppler parameter from the first and second receive signals, respectively, are generated. The first and second Doppler values are combined, where the combination is responsive to a function selected from the group consisting of: addition, multiplication, division and combinations thereof An image responsive to the combination is generated.

In a third aspect, yet another medical diagnostic ultrasound method for Doppler processing is provided. A plurality of pulses are transmitted along a first scan line. The plurality comprises a flow sample count. A plurality of samples responsive to the plurality of pulses, respectively, are received. The plurality of samples are separated into first and second sets of receive signals responsive to respective first and second frequency bands where a number of the first and second receive signals for each depth is at least about twice the flow sample count for a single frequency band. First and second sets of Doppler values of a same parameter responsive to the first and second sets of receive signals, respectively, are determined. The first and second sets of Doppler values are combined, wherein the combination increases an accuracy of the combined Doppler values.

In a fourth aspect, a medical diagnostic ultrasound method for Doppler processing is provided. First and second Doppler velocity values at first and second frequency bands, respectively, are obtained where the first frequency band is different than the second frequency band. First and second Doppler energy values at the first and second frequency bands, respectively, are also obtained. The application of an algorithm to extend the conventional maximum velocity limit associated with at least one of the first and second Doppler velocity values is determined in response to at least one of the first and second Doppler energy values.

Further aspects and advantages are discussed below in conjunction with the preferred embodiments.

DETAILED DESCRIPTION OF THE INVENTION

In preferred embodiments described below, the bandwidth of the ultrasound system may be more effectively used to generate accurate Doppler images. The spectral bandwidth of an ultrasound system and associated phased array transducer is proportional to information content. Narrowband pulses are common in color flow mapping (i.e. Doppler imaging), since narrowband pulses may improve the signal-to-noise ratio (SNR). Due to transmit voltage limits, narrowband pulses can increase the transmitted power as compared to broadband, shorter pulses. Narrowband pulses are also common in gated spectral Doppler systems, since the pulse length is usually matched to the user's selected gate size and increased pulse lengths can improve the SNR. Further, when the SNR is sufficient, a narrowband pulse may still be preferred over a broadband pulse since the axial resolution of a broadband pulse can exceed the lateral resolution of a system. Sample volumes with comparable resolutions along orthogonal dimensions are often preferred.

The information made available to a motion detection system is increased by selectively processing received signals from two or more frequency bands. The transmitted pulses may be composed of a single broadband spectrum or single or multiple narrow frequency band spectra. To acquire the greater information content, separate Doppler estimates or values are obtained at the two or more received frequency bands. This additional information may be used to improve the accuracy and precision of Doppler images and better differentiate tissue from fluid flow.

This process effectively increases the flow sample count for Doppler processing. The number of pulses transmitted along any one scan line is called the flow sample count (FSC). These multiple transmissions result in an ensemble or set of received signals for estimating motion at each depth along the scan line. The received signals are filtered to isolate information at two or more different frequency bands, such as at, including at least some of, or within the transmitted band of frequencies (i.e. the fundamental frequency band) or at or within a harmonic band of the fundamental band of frequencies. As used herein, harmonic broadly includes integer harmonics (e.g. the second, third, fourth . . . harmonic), fractional sub-harmonics (e.g. $\frac{1}{2}$ harmonic) and fractional ultra-harmonics (e.g. $\frac{3}{2}$ harmonic). The isolated receive signals for each frequency band are separately used to estimate motion, such as velocity, energy, and/or variance of motion.

The accuracy and precision of each parameter estimate is limited by the FSC. By generating Doppler values for each frequency band, the estimation of motion may be improved without any additional firings. Combining the ensembles and/or providing a selection process based upon thresholds increases the accuracy and effective FSC for each Doppler value used to generate an image.

Figure 1:
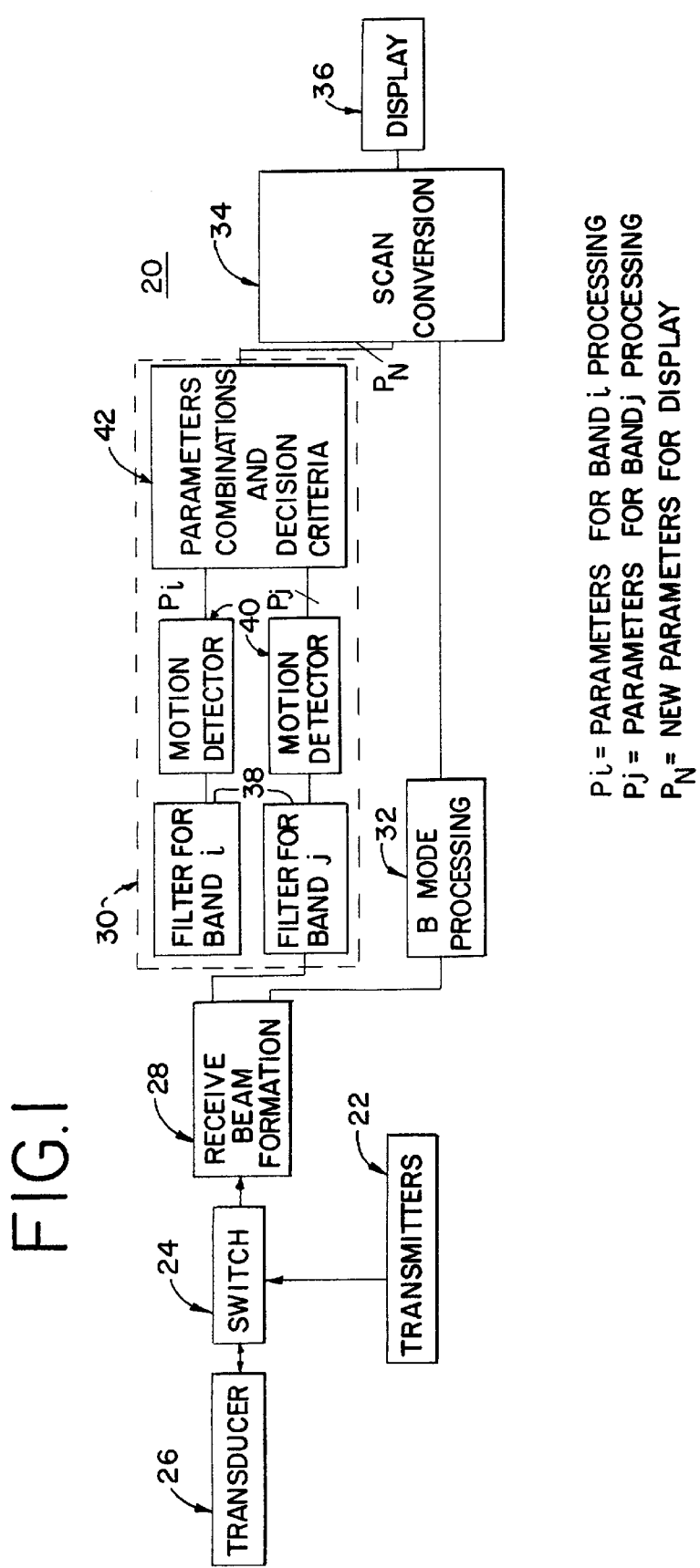
FIG. 1 is a block diagram of one embodiment of a preferred medical diagnostic ultrasound system for Doppler processing.

Referring to FIG. 1, one preferred embodiment of a medical diagnostic ultrasound system for implementing the Doppler processing and combination and/or selection discussed above is shown generally at 20. The ultrasound system 20 comprises a transmitter 22, a switch 24, a transducer 26, a receive beamformer 28, a motion detection system 30, a B-mode processor 32, a scan converter 34 and a display 36. These components are connected as shown in FIG. 1.

The system 20 generally comprises one of any conventional ultrasound systems, such as ultrasound systems manufactured by Acuson Corporation under the trade names 128XP, Aspen, and Sequoia. Other ultrasound systems by other manufacturers may be used, including digital or analog systems currently manufactured and systems yet to be manufactured or designed. These ultrasound systems are designed or altered to provide the motion detection system 30 discussed herein. As discussed above, motion detection is performed for each of two or more frequency bands.

The transmitters 22 comprise transmitters for generating appropriately delayed and apodized waveforms for an aperture of the transducer 26. Preferably, the transmitters 22 are operable to generate waveforms for transmit pulses with a signal content composed of one frequency band or multiple frequency bands. The transmitters 22 may comprise unipolar or bipolar gate burst devices, analog or digital devices, and/or programmable devices. For example, the transmitters described in U.S. Pat. Nos. 5,046,500 and 5,675,554 are used.

The waveforms generated by the transmitters 22 are switched to the transducer 26 by switch 24. The switch 24 comprises a multiplexer or other device for separating the transmitter 22 from the receive beamformer 28. The transducer 26 preferably comprises a phased array transducer for imaging in one or more of various formats. The transducer may be a 1D, 1.5D, or 2D phased array transducer.

The transducer 26 generates a transmit pulse in response to the waveforms. The pulse comprises an ultrasonic wave focused along one or more scan lines.

Figure 3:
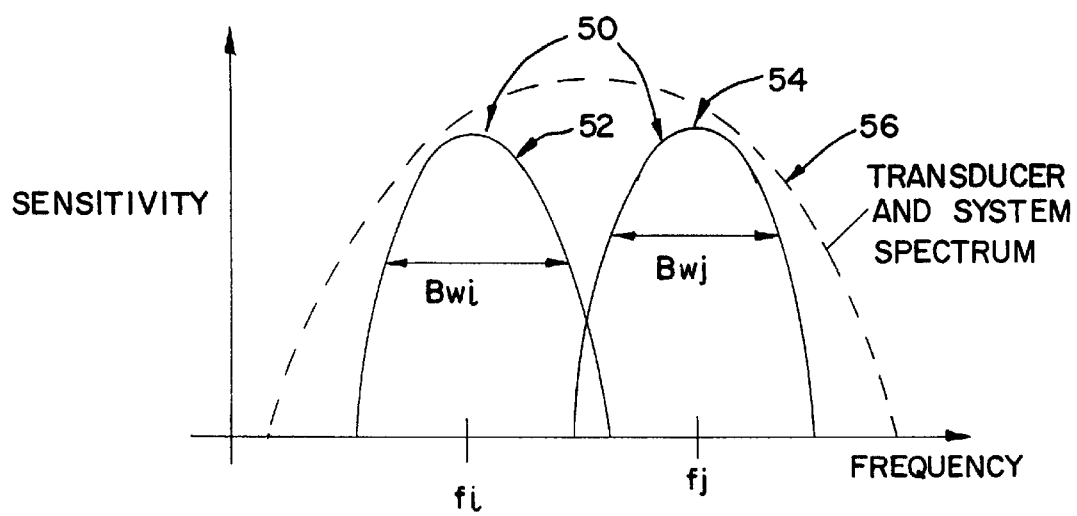
FIG. 3 is a graphical representation of a transducer and system spectral magnitude response and two receive frequency bands.

The transmit pulse is characterized by one or more bandwidths and spectral distributions. For example and referring to FIG. 3, one possible frequency distribution of a transmitted pulse is shown at 50. The frequency distribution 50 includes two more narrow band frequency distributions 52 and 54. Each more narrow frequency band 52 and 54 is defined by a center frequency $f_x$ and a bandwidth $BW_x$. The frequency distribution 50 of the transmitted pulse, including the more narrow frequency bands 52 and 54, is within a bandwidth 56 of the transducer 26 and the imaging system 20. The bandwidth may be defined at any level relative to the peak sensitivity, such as −3 dB or −6.82 dB. Different spectral shapes (e.g. fall off) and distributions may be used, including transmitting only at one dominant single frequency band. For example, a transducer with a relative bandwidth of 80 percent (e.g. 4 MHz centered about 5 MHz) is used to transmit a pulse with a bandwidth of about 1 MHz centered about 4 MHz. For higher frequency imaging and improved lateral resolution, a higher center frequency may be used. Broadband pulses may also be used. Frequencies within the transmitted bandwidth comprise fundamental frequencies.

The wave propagates through and reflects off of structures within a target. The target may comprise one or more of various fluids, tissues and optionally contrast agents.

Referring to FIG. 1, the transducer 26 converts reflected echoes of the ultrasonic wave into electrical signals. For each transmission, the echoes are sampled along the scan line by the receive beamformer 28. The receive beamformer 28 comprises a digital or analog beamformer for converting the electrical signals of multiple channels in the transducer 26 into receive samples representing the target along the scan line. These receive samples correspond to range gates or depth. The receive samples may comprise digital or analog data.

This transmission and reception process is repeated two or more times along each scan line to generate an ensemble comprising a number of received samples equaling the FSC for each depth of interest along one or more scan lines.

The received samples are optionally passed to the B-mode processor 32 for detection. The detected information is scan converted by scan converter 34 for display of an image on the display 36.

The received samples are also provided to the motion detection system 30. The motion detection system 30 comprises two filters 38 and two Doppler processors 40 in parallel data paths connected to a combination and/or selection processor 42.

The filters 38 comprise bandpass, high pass, low pass or other filters for isolating receive signals at a selected frequency band from the received samples. Each filter 38 isolates information at a different frequency band. In alternative embodiments, only one filter 38 and a memory are provided for sequentially isolating the receive signals at two or more different frequency bands.

Figure 2:
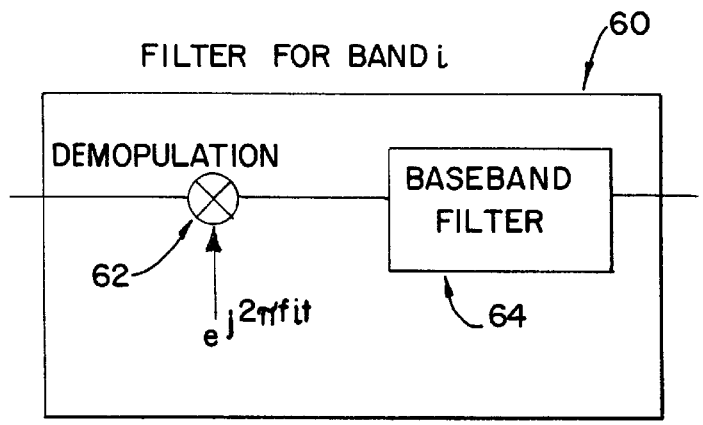
FIG. 2 is a block diagram of one embodiment of a preferred filter of the ultrasound system of FIG. 1.

Referring to FIG. 2, a preferred embodiment of each filter 38 is shown at 60. The filter 60 comprises a demodulator 62 and a baseband filter 64. The demodulator shifts the frequencies of interest into the passband of the baseband filter 64. Preferably, the baseband filter 64 is characterized by a center of the passband being at DC (i.e., zero frequency), such as a low pass filter. The baseband filter 64 may have a programmable pass band. Demodulation down to a frequency other than DC and a baseband filter with a passband centered at a frequency other than zero may also be used.

The frequency used for demodulation may change as a function of depth, such as to account for propagation characteristics of the transmit pulse. Likewise, the baseband filter characteristics may change as a function of depth and/or scan line position. The baseband filter may comprise a real or complex filter for providing variable filter impulse responses for changing the bandwidth, center frequency and/or roll-off. If nonlinear phase modulated pulses are transmitted, as with many coded waveforms, complex filtering can be used to decode the waveforms accurately. Furthermore, the filtering may change as a function of the receive beam for imaging modes that use more than one receive beam per transmit beam.

Referring to FIG. 1, the filters 38 isolate receive signals at two or more different frequency bands. The two or more receive frequency bands may comprise: (1) components substantially within the same frequency components as transmitted, where the transmitted pulse may be composed of a single broadband spectrum or separate narrowband spectra; (2) one receive band substantially the same as or within the transmitted frequency band and one receive band with signal components originating from nonlinear scattering, reflection, or propagation of ultrasound; or (3) both receive bands containing frequency components substantially not present in the transmitted pulse. For example and referring to FIG. 3, the filters 38 separately isolate receive signals at the two more narrow frequency bands 52 and 54.

The isolated receive signals at the two different frequency bands are provided to the Doppler processors 40. The Doppler processors 40 comprise motion detectors or signal processors incorporating Doppler processing algorithms or other motion detection algorithms, such as auto-correlation algorithms, cross-correlation algorithms or Fast Fourier transform algorithms. Preferably, at least two Doppler processing paths or processors 40 are provided for processing the receive signals at the two frequency bands in parallel. In alternative embodiments, one Doppler processor sequentially processes the receive signals to detect motion parameters.

Figure 4:
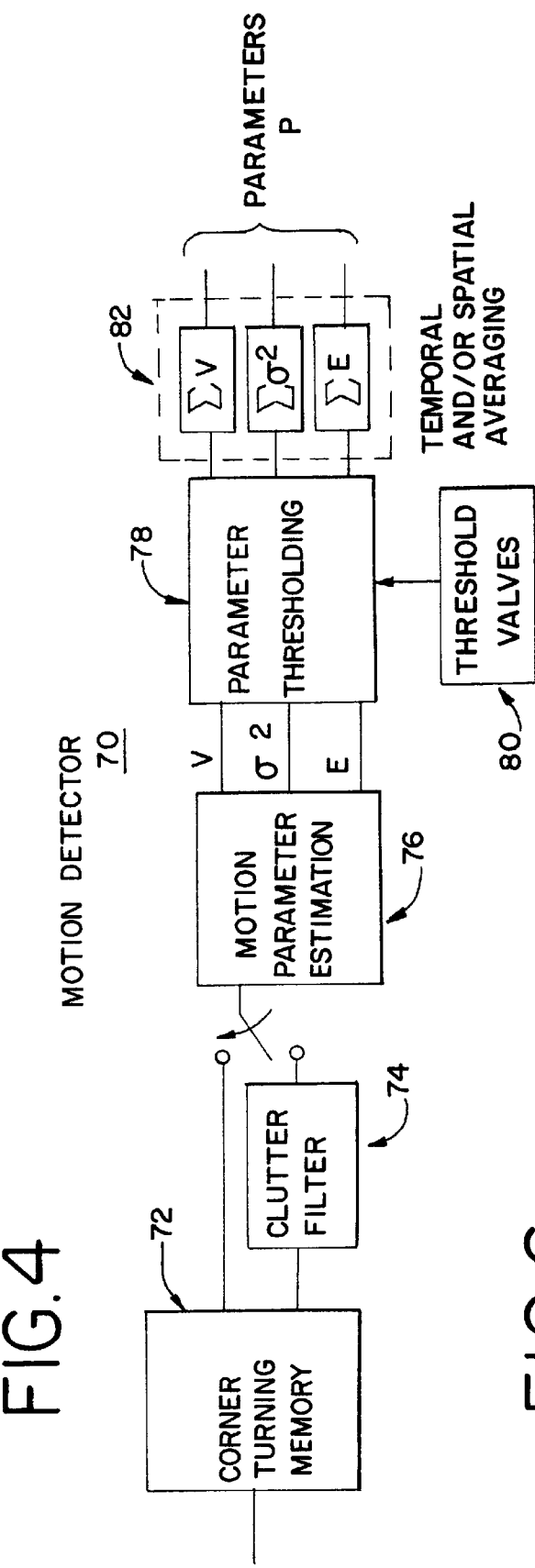
FIG. 4 is a block diagram of one embodiment of a preferred motion detector of the ultrasound system of FIG. 1.

Referring to FIG. 4, a block diagram of one preferred embodiment of the Doppler processors 40 and associated hardware is shown at 70. The Doppler processor and associated hardware 70 comprises a corner turning memory 72, an optional clutter filter 74, Doppler processor 76, optional parameter thresholder 78 and associated threshold controller 80, and optional temporal and/or spatial filter 82.

A set of received signals from two or more transmitted pulses are stored in the corner turning memory 72. Corner turning memory comprises a buffer, RAM or other memory device for collecting receive signals until the desired FSC is reached.

Upon accumulation of FSC number of pulses, the clutter filter 74 is optionally applied to remove unwanted frequency components due to such sources as stationary tissue or slowly moving blood vessel walls. The clutter filter 74 preferably comprises a high pass filter and may incorporate FIR, IIR, or other techniques for implementation. Low pass or bandpass filters may also be used. Adaptive clutter filters that vary filter characteristics on a sample-by-sample basis within the image using measured signal characteristics may also be used. Clutter filtering may be bypassed, such as for estimating tissue motion for Doppler tissue imaging or estimating clutter signal characteristics. Estimating clutter signal characteristics may be useful for adaptive clutter suppression techniques. Furthermore and referring to FIGS. 1 and 4, with the use of two separate Doppler processors 40, the two clutter filters 74 may be applied independent of each other. For example, one clutter filter 74 has an impulse response with a lower cut-off frequency than the other clutter filter 74. Independent application is useful since nonlinear propagation and other mechanisms for generating harmonic energy may produce signals associated with broader bandwidths than the transmitted bandwidth. This broader bandwidth improves resolution and thus can reduce deleterious clutter. A path that processes harmonic energy may independently set the clutter filters 74 and thresholds to improve motion detection accuracy.

The output of the clutter filter 74 or the corner turning memory 72 is provided to the Doppler processor 76. The Doppler processor 76 estimates Doppler values for one or more parameters for each depth along a scan line from the ensemble of received signals. For example, Doppler values are provided for each of mean velocity, variance, and energy parameters. Other Doppler parameters may be estimated.

The estimated Doppler values are optionally thresholded by the parameter thresholder 78. The parameter thresholder 78 comprises a processor or look-up table for outputting Doppler values that are larger or smaller than a threshold provided by the threshold controller 80. Different, including no, thresholds may be applied to Doppler values of each different parameter. Furthermore, Doppler values of one parameter may be changed as a function of the amplitude of Doppler values associated with a different parameter.

The Doppler values may also be filtered, such as temporal and/or spatial filtering by averaging or other functions. This filtering may be performed on Doppler values of one parameter independent of Doppler values of another parameter. Thresholding may be performed prior to averaging and vice versa.

The output of the Doppler processor and associated hardware 70 comprises Doppler values representing a spatial location along a scan line and one or more Doppler parameters. Doppler values for two different frequency bands are provided for each spatial location.

Referring to FIG. 1, the Doppler values are provided to the combination and/or selection processor 42. The combination and/or selection processor 42 comprises one or more general processors with software, one or more digital signal processors, dedicated hardware, one or more look-up tables or other devices for combining and/or selecting Doppler values. In one preferred embodiment, the combination and/or selection processor 42 both combines and selects Doppler values as discussed below. In alternative embodiments, the combination and/or selection processor 42 either combines or selects Doppler values. In yet another alternative embodiment, a separate processor is provided for each of combination and selection.

Figure 5:
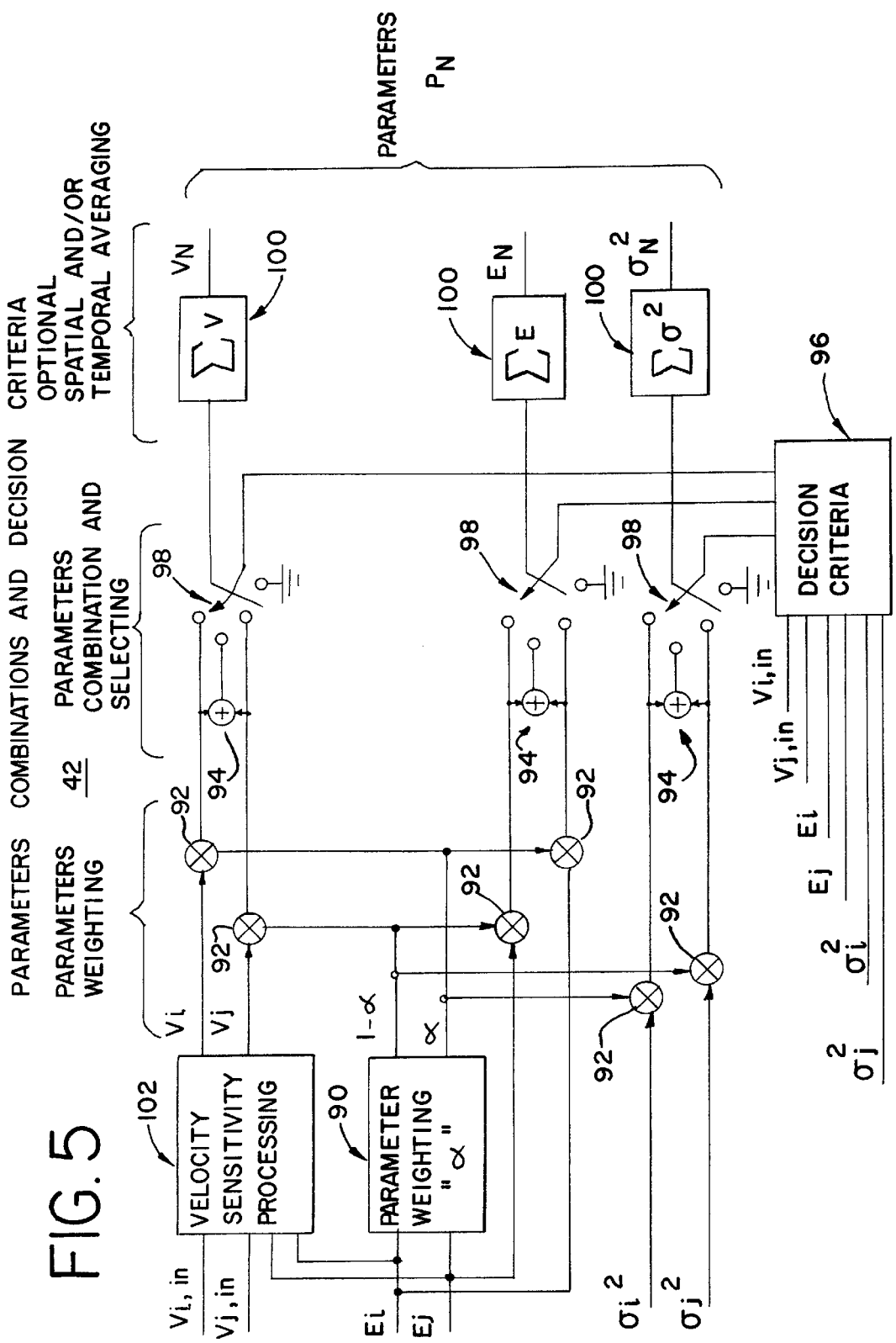
FIG. 5 is a graphical representation of one preferred embodiment of selection and combination processing performed by the ultrasound system of FIG. 1.

Referring to FIG. 5, a graphical representation of the combination and selection performed by the combination and/or selection processor 42 is shown. Scaling of Doppler values, such as before or after combination, may be performed, but is not shown here for simplicity.

In one preferred embodiment, Doppler values for each frequency band representing each of velocity, energy and variance parameters are provided to the combination and/or selection processor 42. Fewer parameters may be provided. The Doppler values representing the velocity parameter may be processed for velocity sensitivity as discussed herein. Alternatively, the velocities are not processed to determine velocities above the conventional maximum detectable limits.

Doppler values for one or more parameters representing information at different frequency bands for the same spatial location are combined by the combination and/or selection processor 42. The combination preferably comprises averaging the Doppler values. In alternative embodiments, other combinations, such as functions including addition, division or multiplication, may be used.

FIG. 5 represents the preferred averaging embodiment. In this embodiment, the Doppler values at each frequency band are weighted. Given two different frequency bands, two Doppler values for each parameter at each spatial location are averaged as a function of the relative weights or coefficients $\alpha$ and $1-\alpha$. The coefficients may be selected as a function of the imaging application or otherwise set. For example, each coefficient is set to 0.5 for averaging the Doppler values equally.

In a preferred alternative embodiment, the coefficients are adaptively selected as a function of one or more Doppler values, such as represented by parameter weighting block 90. For example, the coefficients used to weight the different Doppler values are determined as a function of the two input energy estimates. Preferably, estimates generated under high SNR conditions are weighted more heavily than those estimates that were generated under low SNR conditions. If a velocity or variance was estimated under poor SNR conditions, the Doppler value may not be accurate. Energy estimates may provide a measure of SNR.

The coefficient, a, may be fixed at 0.5 within a scale of 0 to 0.5 if the energy between the estimates at different frequency bands are similar or within a range of each other. Other functions of the two energy Doppler values may be defined for selecting the coefficients. For example, the weighting coefficient, $\alpha$, may be linear over the dynamic range of the received energy values. In yet other alternatives, Doppler values representing parameters other than energy are used to select the coefficients, or different parameters may be used for determining coefficients applied to fewer than all of the other Doppler parameters.

Figure 6:
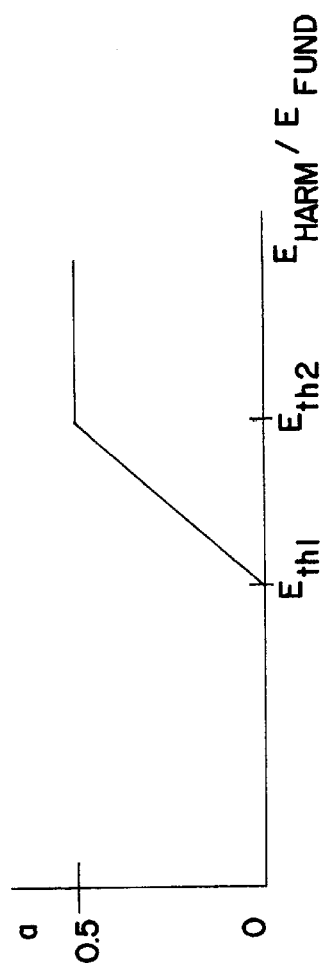
FIG. 6 is a graphical representation of a non-linear coefficient selection function.

As an alternative to linear selection of the coefficients, non-linear selection may be provided. For example and referring to FIG. 6, the coefficient, $\alpha$, is selected as a function of a ratio of the two energies at the different frequency bands, such as fundamental and harmonic frequency bands. If the ratio is below a threshold $E_{th1}$, or above a threshold $E_{th2}$, the coefficient is constant at 0 and 0.5, respectively. Between these two thresholds, a linear or nonlinear relationship between the coefficient and the energy ratio is used. FIG. 6 shows a linear function between $E_{th1}$ and $E_{th2}$. Experimentation for each clinical application may yield different functions. Energy values for determining the coefficients may be defined for Doppler values at any one or both of the two received frequency bands as the total energy above a noise level. This noise level may be fixed as a function of range, specified for selected application with user control, or automatically measured from data received in the system 20 with all transmitters turned off.

After the coefficients, if any, are determined in parameter weighting block 90, the coefficients are applied to Doppler values of one or more parameters. As shown in FIG. 5, the coefficients are applied to the Doppler values for each parameter by multipliers 92.

The weighted Doppler values at each frequency band are combined. If the coefficients sum to unity, then summing the weighted Doppler values comprises averaging the Doppler values. In this embodiment, generation of the combination data is mathematically represented by:

$$V_{new} = (1-\alpha)V_f + (\alpha)V_i$$

In this preferred embodiment, summers 94 add the weighted Doppler values. In alternative embodiments, coefficients summing to more or less than one may be used. In such alternative embodiments, the resulting combination values may be scaled. In yet other alternative embodiments, weighted or unweighted Doppler values are multiplied with a multiplier or divided with a divider. A look-up table, processor or other devices for implementing various functions may be used.

As shown in FIG. 5, two Doppler values are weighted and combined. More than two Doppler values corresponding to a respective more than two different frequency bands may be combined. Preferably, the SNR associated with each frequency band is adequate. In one embodiment, this combination is mathematically represented by:

$$V_{new} = [\alpha_1 V_1 + \alpha_2 V_2 + \ldots \alpha_N V_N]$$

where $\alpha_i$ are weightings proportional to the energy received at each frequency band. Preferably, the sum of the weightings $\alpha_i$ equals 1.

The combination and/or selection processor 42 selects an appropriate Doppler value, such as the combination Doppler value, as a selection value. As used herein, selection value is broadly interpreted to mean any value used to generate an image, calculate a quantity or otherwise provide diagnostic information to a user, regardless of any processing between generation of the selection value and providing diagnostic information to the user. For example, the selection value comprises a selected Doppler value that is then used to determine a color or RGB value for display.

Switches 98 and decision criteria block 96 select from two or more possible values for one or more parameters. Switches 98 and decision criteria block 96 represent software or hardware for implementing the selection processor 42. In alternative embodiments, the values for selection are provided to the decision criteria block 96 which merely outputs the selected Doppler values.

In one preferred embodiment, the weighted Doppler values, the combination Doppler values, and a null value (i.e. zero) for each parameter are available for selection. In alternative embodiments, different, fewer or more values are available for selection, such as an additional minimum value greater than zero or a maximum value. In yet other alternative embodiments, different sets of values are available for selection for different parameters.

The decision criteria block 96 selects the best available Doppler value for a given parameter for further processing and display. Preferably, the combination value of at least one parameter is available for selection since the sum or average provides a new Doppler value with improved accuracy.

As an example of combination data providing improved accuracy, the carotid is scanned without the use of contrast agents. During the scanning of a carotid, nonlinear propagation of the transmit pulse through tissue generates signals within a band of frequencies around the second harmonic, as well as around the fundamental frequencies. The signal content at the second harmonic frequency band provides a second Doppler value in addition to a Doppler value estimated from receive signals at the fundamental frequency band. Both Doppler values originate from different pulse propagation characteristics due to the different frequency bands. The resulting combination data provides for improved Doppler estimation since the use of two different frequency bands effectively increases the FSC and accuracy.

Selecting between Doppler values at two different frequency bands also increases accuracy. One frequency band may be associated with poor SNR, possibly represented by low energy values, so the availability of the Doppler value at another frequency band may improve accuracy. The Doppler value at this other frequency band may be associated with better SNR, such as associated with high energy values.

The decision criteria block 96 selects the available Doppler values for one or more of the parameters as a function of input Doppler values. The input Doppler values preferably include the Doppler values at each frequency band for each parameter. These Doppler values may comprise the Doppler values before or after being weighted and/or scaled. In alternative embodiments, fewer Doppler values are input into the decision criteria block 96, such as only Doppler energy or variance values. In yet other alternative embodiments, the combination values are input into the decision criteria block 96.

The decision criteria block 96 selects the Doppler values for further processing by controlling the switches 98. One or more of the input Doppler values are used to select the Doppler values for further processing. For example, the input Doppler energies are examined to determine that estimates from both frequency bands have adequate SNR. The input Doppler velocities are examined for non-zero flow. In this situation, the combination data may be selected as the imaging value. If one input Doppler velocity was low or zero, the null value may be selected. Alternatively, the Doppler values associated with one frequency band are always selected unless the energy and velocity Doppler values at that frequency band show good SNR and high velocity, then combination data may be selected. Other combinations and defaults may be used for selecting the selected value. Different thresholds for selecting may be used, such as thresholds developed through experimentation for different types of imaging or different imaging applications.

The selected value or values are optionally spatially and/or temporal filtered by filters 100. Furthermore, the selected values may be scaled. Referring to FIG. 1, the imaging values are provided to the scan converter 34. The scan converter 34 reformats the imaging values as needed. Doppler values of one or more parameters for imaging are used to determine display data for generating a Doppler image on the display 36. The Doppler image may be combined with a B-mode or another Doppler image or may be displayed alone.

Preferably, the operation of the system of FIG. 1 or other systems for combination and/or selection of Doppler values at two or more different frequency bands is performed as a function of the imaging application. Imaging applications include imaging a target with or without contrast agents. Contrast agents are injected into a target to provide enhanced echo signals at one or both of the fundamental and harmonic frequency bands. Harmonic imaging may be performed without contrast agents. Tissue provides a non-linear response to the transmitted pulse. For harmonic imaging of tissue, the target is maintained free of added contrast agent throughout an entire imaging session. Ultrasound examinations are typically performed in a discrete imaging session of ¼ to 1 hour.

The following examples show the contribution of combination and/or selection to the display of two-dimensional color flow imaging with improved accuracy and tissue/clutter differentiation. In a first example, blood vessel imaging using the fundamental and second harmonic frequency bands without contrast agents in the target is performed. A sample volume within a blood vessel reflects energy in the transmitted fundamental frequency band and energy accumulated around the second harmonic frequency band of the fundamental energy. The clutter filters 74 remove clutter from the nearby vessel walls and other clutter signals in both frequency bands. The thresholders 78 determine that all the Doppler values are associated with valid flow (i.e., exhibit adequate SNR). The combination and/or selection processor 42 sets the weighting coefficient to 0.5 since the energy estimates are similar in magnitude. The decision criteria block 96 selects the combination data for one or more parameters since the Doppler energy values at each frequency band are strong and the Doppler velocity values are nonzero. By using combined data from two frequency bands, the imaging value provides reduced estimation variability (i.e. effectively higher FSC). If the Doppler values at the second harmonic frequency band are unacceptable due to a poor SNR (e.g., low energy) and optionally low velocity, the Doppler value at the fundamental frequency band is selected.

In a second example, imaging at the fundamental and second harmonic frequency bands without contrast agents of a blood vessel and tissue distal to the blood vessel is provided. A conventional system may inaccurately display a velocity estimate at the tissue sample volume, despite the lack of any blood flow. This problem may be due to acoustic reverberations where multiple reflections have delayed the reception of a velocity estimate from the center of a vessel, such that the estimate results in erroneous display of information distal to the blood vessel. Since tissue generated signals at harmonic frequencies may originate, reflect, and propagate along an effectively different path to the same point in space than signals at the transmitted fundamental frequency band, acoustic reverberations of the signals at harmonic frequencies may be significantly diminished. After clutter filtering, the harmonic frequency band Doppler value more accurately indicates a lack of flow. In this scenario, the decision criteria block 96 is provided two strong Doppler energy values, one nonzero large velocity estimate for the fundamental frequency band, and one low velocity estimate (or zero) for the harmonic frequency band. Since the harmonic frequency band Doppler values represent the sample volume as clutter (i.e., low or zero velocity, and possibly low variance) and indicate adequate SNR (e.g. high energy), the image value is selected as a null value, reducing the bleed over of inaccurate velocity estimates at sample volumes representing tissue.

Since the level of signals at the second harmonic generated from tissue propagation can be 20–30 dB below the peak signal level at the fundamental frequency band, a two dimensional color flow image generated solely based on second harmonic energy may have inferior SNR over a practical display area. Thus, generating second harmonic color flow images may be impractical without contrast agents, but the available energy from nonlinear propagation can be used to complement the detection process of energy at fundamental frequencies by using combination data.

In a third example, signals at fundamental and harmonic frequency bands are used to image contrast agents in a target. When imaging with contrast agents, processing signals at the second harmonic frequency band is preferred. Second harmonic energy from contrast agents increases agent specificity. Since the flow-to-clutter ratio of signals at the second harmonic frequency band can be larger than the flow-to-clutter ratio of signals at the fundamental frequency band, selecting the second harmonic frequency band may provide improved clutter and flash suppression. Doppler values at the harmonic and fundamental frequency bands are averaged, or the combination selected, when the Doppler values at the harmonic frequency band are "good," such as a high energy, and optionally high variance and non-zero velocity. The Doppler values at the fundamental frequency are selectively included without reducing the benefits of increased specificity and sensitivity when harmonics are the preferred imaging mode. Since the harmonic image is preferred in this application, Doppler values at the fundamental frequency band are not included in the final output image (e.g. Doppler values at the second harmonic frequency band are selected instead of the combination data) when the Doppler values at the second harmonic are "poor," such as associated with a low SNR.

In a fourth example, signals received at fundamental and harmonic frequency bands are used to image contrast agents in a target after transmitting at one or more frequency bands. Imaging at the second harmonic or a sub-harmonic frequency of the fundamental may be preferred. As was described in the previous example three, harmonic frequency information may improve agent specificity and "good" harmonic estimates may be identified based on high energy levels and optionally other parameters, such as high variance and/or non-zero velocity. In this example, Doppler values, preferably energy values, at the two frequency bands are multiplied together and made available at the switches 98. When the Doppler values from both frequency bands are "good" values, the decision criteria block 96 selects the multiplied combination. The multiplied combination effectively increases specificity of harmonic signals since the multiplication of the two like parameters can be designed to yield a result that is larger than the summation of the two values. If the harmonic frequency parameter is a "good" estimate and the fundamental frequency parameter is a "poor" estimate, the value of the harmonic frequency is selected instead of the multiplied combination. A "poor" fundamental estimate may be identified based on low variance and/or low velocity. Values at the fundamental frequency band may be more significantly corrupted by clutter than is the case with the harmonic frequency estimate. If both frequency band estimates are "poor" the null parameter is selected with the switches 98.

Harmonic frequency bands other than the second harmonic may be used. For example, signals at a sub-harmonic frequency band are isolated. For sub-harmonics, the transmit pulse may include some energy at the sub-harmonic frequency band, such as seeding the desired sub-harmonic frequency band with energy in the transmit pulse sufficient to provide adequate SNR. See for example, U.S. application Ser. No. 09/282,603, filed herewith, by Chuck Bradley et. al.

The Doppler values at two or more frequency bands may also be used to extend the range of detectable Doppler velocities. Referring to FIG. 5, the velocity sensitivity processing block 102 is optionally provided, such as representing a general processor or digital signal processor for applying an algorithm to extend the maximum detectable velocity limit. Where provided, the velocity sensitivity processing block 102 applies any one of various algorithms, such as the algorithms discussed in the Background Section.

In a preferred alternative embodiment, the algorithm described in Appendix A by H. J. Hitzpon et al. in "A New Pulsed Wave Doppler Ultrasound System to Measure Blood Velocities Beyond the Nyquist Limit", IEEE Transactions on Ultrasonics, Ferroelectrics, and Frequency Control, Vol. 42, No. 2, March 1995 is used. This algorithm to extend the detectable velocity limit determines the Doppler velocity values $v_i$ and $v_j$ as:

$$v_i = v_{i,in} + 2k_i v_{i,max}$$

$$v_j = v_{j,in} 30\ 2k_j v_{j,max}$$

where $v_{i,max}$ and $v_{j,max}$ are the maximum unaliased velocity limits for each independently processed frequency band, and $k_i$ and $k_j$ are the minimum integers, including zero, where:

$k_i$ is an element of the set $\{-\text{floor}(f_i/f_j - f_i)), \text{floor}(f_i/f_j - f_i))\}$; and $k_j$ is an element of the set $\{-\text{ceil}(f_i/f_j - f_i)), \text{ceil}(f_i/f_j - f_i))\}$ under the constraint that the absolute value of $v_i - v_j$ is minimized for the possible set of integers. The term "floor" refers to the integer nearest negative infinity and the term "ceil" refers to the integer nearest positive infinity.

This algorithm determines whether the Doppler values are aliased. If aliased, then the algorithm extends the alias limit to detect larger velocities. If not aliased, the algorithm does not alter the Doppler velocities.

To further improve Doppler velocity value estimates using two frequency bands, the energy estimates are used to selectively disable the algorithm. If one of the Doppler energy values at the two different frequency bands corresponding to the Doppler velocity values is below a threshold indicative of adequate SNR, then the algorithm to extend the limit is bypassed (i.e. not applied) regardless of whether the velocities are within or beyond the conventional limits. Using energy to determine application of the algorithm avoids displaying poor velocity estimates due to poor SNR or significant suppression by the clutter filters 74.

While the invention has been described above by reference to various embodiments, it will be understood that many changes and modifications can be made without departing from the scope of the invention. For example, selection without combination may be used to improve accuracy, or combination without selection may be used to improve accuracy. Clutter filtering, spatial filtering, temporal filtering, application of the algorithm to extend the maximum velocity limits and other processing may be bypassed or not provided. Various techniques for estimating motion may be used.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A medical diagnostic ultrasound method for Doppler processing, the method comprising the steps of:
   (a) obtaining first and second receive signals at first and second frequency bands, respectively, the first frequency band different than the second frequency band;
   (b) determining first and second Doppler values of a same type of Doppler parameter from the first and second receive signals, respectively;
   (c) selecting a value from a group of two or more of: the first Doppler value, the second Doppler value and a third Doppler value that is a combination of the first and second Doppler values, the first, second and third values associated with a substantially same location; and
   (d) generating a Doppler display responsive to the selected value.

2. The method of claim 1 wherein step (c) comprises:
selecting from the group of all of: the first Doppler value, the second Doppler value, the third Doppler value, and a null value.

3. The method of claim 2 wherein step (c) comprises:
selecting the null value where a first Doppler velocity is larger than a first threshold and a second Doppler velocity is less than a second threshold.

4. The method of claim 3 wherein step (c) further comprises:
selecting the null value where a first Doppler energy is larger than a third threshold and a second Doppler energy is larger than a fourth threshold.

5. The method of claim 2 wherein step (c) comprises:
selecting in response to the first and second Doppler values.

6. The method of claim 1 wherein step (c) comprises:
selecting in response to a selection value from the group consisting of: the first Doppler value, the second Doppler value, a Doppler energy value, a Doppler velocity value, a Doppler variance value and combinations thereof.

7. The method of claim 6 wherein step (c) comprises:
selecting the third Doppler value where first and second Doppler energies responsive to the first and second frequency bands are both larger than a threshold.

8. The method of claim 6 wherein step (c) comprises:
selecting the first Doppler value where a first Doppler energy responsive to the first frequency band is larger than a threshold and a second Doppler energy responsive to the second frequency band is less than the threshold.

9. The method of claim 6 wherein step (c) comprises:
selecting the second Doppler value in response to the selection value from the group consisting of: the second Doppler value, a Doppler energy value at the second frequency band, and a Doppler variance value at the second frequency band.

10. The method of claim 1 wherein step (c) comprises:
selecting one of the third Doppler value and the second Doppler value in response to one of a Doppler energy value at the second frequency band and a Doppler variance value at the second frequency band.

11. The method of claim 1 further comprising:
(e) clutter filtering at least one of the first and second receive signals prior to step (b).

12. The method of claim 1 wherein:
step (c) comprises selecting the third Doppler value; and
the third Doppler value being an average of the first and second Doppler values.

13. The method of claim 1:
wherein step (b) comprises obtaining first and second Doppler velocity values at the first and second frequency bands, respectively;
further comprising:
(e) obtaining first and second Doppler energy values at the first and second frequency bands, respectively; and
(f) determining application of an algorithm to extend the maximum detectable velocity limit associated with at least one of the first and second Doppler velocity values in response to at least one of the first and second Doppler energy values.

14. The method of claim 1 wherein the first and second receive signals are responsive to ultrasonic waves in a target and the target is kept substantially free of contrast agents during an entire imaging session.

15. The method of claim 1 wherein the first and second receive signals are responsive to ultrasonic waves in a target and target comprises contrast agents.

16. The method of claim 1 wherein the first and second Doppler values comprise Doppler velocity values.

17. The method of claim 1:

further comprising:

(e) transmitting a first pulse characterized by a first bandwidth; and wherein the first and second frequency bands are within the first bandwidth and the first and second receive signals are responsive to the first pulse.

18. The method of claim 1:

further comprising:

(e) transmitting a first pulse at a fundamental frequency band; and wherein the first frequency band comprises at least some of the transmitted fundamental frequency band, the second frequency band comprises a frequency band at a harmonic of the fundamental frequency band, and the first and second receive signals are responsive to the first pulse.

19. The method of claim 1 wherein:

step (c) comprises selecting the third Doppler value; and the third Doppler value being responsive to an addition of the first and second Doppler values.

20. The method of claim 1 wherein:

step (c) comprises selecting the third Doppler value; and the third Doppler value being responsive to a multiplication of the first and second Doppler values.

21. The method of claim 1 wherein:

step (c) comprises selecting the third Doppler value; and the third Doppler value being responsive to a division of the first and second Doppler values.

22. The method of claim 1 wherein the first and second Doppler values comprises Doppler energy values.

23. The method of claim 1 wherein the first and second Doppler values comprises Doppler variance values.

24. The method of claim 1 further comprising:

(e) transmitting a first pulse at a fundamental frequency band;

wherein the first frequency band substantially comprise a harmonic band of the fundamental frequency band, the second frequency band substantially comprises a harmonic band of the fundamental frequency band, and the first and second receive signals are responsive to the first pulse.

25. The method of claim 1 further comprising:

(e) transmitting a first pulse with at least two fundamental frequency bands;

wherein the first and second frequency bands comprise the at least two transmitted fundamental frequency bands and the first and second receive signals are responsive to the first pulse.

26. The method of claim 1 further comprising:

(e) transmitting a first pulse with at least two fundamental frequency bands;

wherein the first and second frequency bands substantially comprises harmonic bands, and the first and at least second receive signals are responsive to the first pulse.

27. The method of claim 1 wherein step (b) comprises processing of one of autocorrelation, cross-correlation, and Fast Fourier Transform.

28. A medical diagnostic ultrasound system for Doppler processing, the system comprising:

a filter for obtaining first and second receive signals at first and second frequency bands, respectively, the first frequency band different than the second frequency band;

at least one Doppler processor operatively connected to the filter for determining first and second Doppler values of a same type of Doppler parameter from the first and second receive signals, respectively;

a selection processor operatively connected to the at least one Doppler processor for selecting a selected value from a group of two or more of: the first Doppler value, the second Doppler value and a third Doppler value that is a combination of the first and second Doppler values, the first, second and third values associated with a substantially same location; and a display for generating a Doppler image responsive to the selected value.

29. The system of claim 28 wherein the selection processor is operable to select the selected value from the group of all of: the first Doppler value, the second Doppler value, the third Doppler value, and a null value.

30. The system of claim 28 further comprising a clutter filter for filtering at least one of the first and second receive signals.

31. The system of claim 28 further comprising a summer for generating the third Doppler value, wherein the selection processor selects the third Doppler value.

32. The system of claim 28:

wherein the at least one Doppler processor is operable to generate first and second Doppler velocity values at the first and second frequency bands, respectively and generate first and second Doppler energy values at the first and second frequency bands, respectively; and further comprising an algorithm processor for determining application of an algorithm to extend the maximum detectable velocity limit associated with at least one of the first and second Doppler velocity values in response to at least one of the first and second Doppler energy values.

33. The system of claim 28 wherein the at least one Doppler processor comprises two Doppler processors in parallel paths.

34. The system of claim 28 further comprising a multiplier for generating the third Doppler value, wherein the selection processor selects the third Doppler value.

35. The system of claim 28 further comprising a divider for generating the third Doppler value, wherein the selection processor selects the third Doppler value.

36. A medical diagnostic ultrasound method for Doppler processing, the method comprising the steps of:

(a) obtaining first and second receive signals at first and second frequency bands, respectively, the first frequency band different than the second frequency band;

(b) generating first and second Doppler values of a same type of Doppler parameter from the first and second receive signals, respectively;

(c) combining the first and second Doppler values, the combination being responsive to at least one of addition, multiplication, averaging, and division functions; and (d) generating an image responsive to the combination of step (c).

37. The method of claim 36 further comprising:
(e) selecting the combination of step (c) from a group consisting of the combination of step (c) and at least one of the first Doppler value, the second Doppler value, a maximum Doppler value, a minimum Doppler value, and a null value.

38. The method of claim 37 wherein step (e) comprises:
selecting in response to a value from the group of: the first Doppler value, the second Doppler value, a Doppler energy value, a Doppler velocity value, a Doppler variance value and combinations thereof.

39. The method of claim 36 further comprising:
(e) clutter filtering at least one of the first and second receive signals prior to step (b).

40. The method of claim 36 wherein step (c) comprises:
averaging the first and second Doppler values.

41. The method of claim 36 wherein step (c) comprises:
combining the first and second Doppler values, the combination being responsive to an addition function.

42. The method of claim 36 wherein step (c) comprises:
combining the first and second Doppler values, the combination being responsive to a multiplication function.

43. The method of claim 36 wherein step (c) comprises:
(c1) multiplying the first and second Doppler values by first and second weights, respectively.

44. The method of claim 43 further comprising:
(e) determining the first and second weights as a function of Doppler energy values.

45. The method of claim 36:
wherein step (b) comprises generating first and second Doppler velocity values at the first and second frequency bands, respectively;
further comprising:
(e) generating first and second Doppler energy values at the first and second frequency bands, respectively; and
(f) determining application of an algorithm to extend the maximum detectable velocity limit associated with at least one of the first and second Doppler velocity values in response to at least one of the first and second Doppler energy values.

46. The method of claim 36 wherein the first and second Doppler values comprise Doppler velocity values.

47. The method of claim 36:
further comprising:
(e) transmitting a first pulse characterized by a first bandwidth; and
wherein the first and second frequency bands are within the first bandwidth and the first and second receive signals are responsive to the first pulse.

48. The method of claim 36:
further comprising:
(e) transmitting a first pulse at a fundamental frequency band; and
wherein the first frequency band comprises at least some of the transmitted fundamental frequency band, the second frequency band comprises a frequency band at a harmonic of the fundamental frequency band, and the first and second receive signals are responsive to the first pulse.

49. The method of claim 36 wherein the first and second receive signals are responsive to ultrasonic waves in a target and the target is kept substantially free of contrast agents during an entire imaging session.

50. The method of claim 36 wherein the first and second receive signals are responsive to ultrasonic waves in a target and target comprises contrast agents.

51. The method of claim 36 wherein the first and second Doppler values comprise Doppler energy values.

52. The method of claim 36 wherein step (c) comprises:
combining the first and second Doppler values, the combination being responsive to a division function.

53. The method of claim 36 further comprising:
(e) transmitting a first pulse at a fundamental frequency band;
wherein the first and second frequency bands substantially comprise harmonic bands of the fundamental frequency band, and the first and second receive signals are responsive to the first pulse.

54. The method of claim 36 further comprising:
(e) transmitting a first pulse with at least two fundamental frequency bands;
wherein the first and second frequency bands comprise fundamental frequency bands substantially within the at least two transmitted fundamental frequency bands, and the first and second receive signals are responsive to the first pulse.

55. The method of claim 36 further comprising:
(e) transmitting a first pulse with at least two fundamental frequency bands;
wherein the first and second frequency bands substantially comprise harmonic bands, and the first and second receive signals are responsive to the first pulse.

56. The method of claim 36 wherein the first and second Doppler values comprise Doppler variance values.

57. A medical diagnostic ultrasound system for Doppler processing, the system comprising:
a filter for obtaining first and second receive signals at first and second frequency bands, respectively, the first frequency band different than the second frequency band;
at least one Doppler processor for generating first and second Doppler values of a same type of Doppler parameter from the first and second receive signals, respectively;
a combination processor for combining the first and second Doppler values, the combination being responsive to at least one of addition, multiplication, averaging and division functions; and
a display for generating an image responsive to the combination of the first and second Doppler values.

58. The system of claim 57 further comprising:
a clutter filter for filtering at least one of the first and second receive signals prior to combination.

59. The system of claim 57 wherein the combination processor is operable to average the first and second Doppler values.

60. The system of claim 57 wherein the combination processor comprises first and second multipliers for multiplying the first and second Doppler values by first and second weights, respectively.

61. The system of claim 60 wherein the combination processor further comprises a weighting processor for determining the first and second weights as a function of Doppler energy values.

62. The system of claim 57:
wherein the at least one Doppler processor is operable to generate first and second Doppler velocity values at the first and second frequency bands, respectively and generate first and second Doppler energy values at the first and second frequency bands, respectively; and
further comprising an algorithm processor for determining application of an algorithm to extend the maximum detectable velocity limit associated with at least one of the first and second Doppler velocity values in response to at least one of the first and second Doppler energy values.

63. The system of claim 57 wherein the combination processor is operable to combine the first and second Doppler values as a function of addition.

64. The system of claim 57 wherein the combination processor is operable to combine the first and second Doppler values as a function of multiplication.

65. The system of claim 57 wherein the combination processor is operable to combine the first and second Doppler values as a function of division.

66. A medical diagnostic ultrasound method for Doppler processing, the method comprising the steps of:
   (a) transmitting a plurality of pulses along a first scan line, the plurality comprising a flow sample count;
   (b) receiving a plurality of samples responsive to the plurality of pulses, respectively;
   (c) separating the plurality of samples into first and second sets of receive signals responsive to respective first and second frequency bands, a number of the first and second receive signals for each depth being at least about twice the flow sample count;
   (d) determining first and second sets of Doppler values of a same parameter responsive to the first and second sets of receive signals, respectively; and
   (e) combining the first and second sets of Doppler values;
   wherein the combination of step (e) increases an accuracy of the combined Doppler values.

67. The method of claim 66 wherein step (e) comprises averaging the values from the first and second sets of Doppler values for each depth.

68. The method of claim 66 wherein step (d) comprises determining first and second sets of Doppler velocities.

69. The method of claim 66 further comprising:
   (f) selecting the combination of step (e) from a group of the combination of step (e) and at least one of the first Doppler value, the second Doppler value, a minimum Doppler value, a maximum Doppler value, and a null value.

70. The method of claim 66 wherein step (e) comprises adding the values from the first and second sets of Doppler values for each depth.

71. The method of claim 66 wherein step (e) comprises multiplying the values from the first and second sets of Doppler values for each depth.

72. The method of claim 66 wherein step (e) comprises dividing the values from the first and second sets of Doppler values for each depth.

73. The method of claim 66 wherein step (d) comprises determining first and second sets of Doppler energies.

74. The method of claim 66 wherein step (d) comprises determining first and second sets of Doppler variances.

75. A medical diagnostic ultrasound method for Doppler processing, the method comprising the steps of:
   (a) obtaining first and second Doppler velocity values at first and second frequency bands, respectively, the first frequency band different than the second frequency band;
   (b) obtaining first and second Doppler energy values at the first and second frequency bands, respectively; and
   (c) determining application of an algorithm to extend the maximum detectable velocity limit associated with at least one of the first and second Doppler velocity values in response to at least one of the first and second Doppler energy values.

76. The method of claim 75 wherein step (c) comprises:
   applying the algorithm where the at least one of the first and second Doppler energy values is larger than a threshold.

77. The method of claim 75 wherein step (c) comprises:
   applying the algorithm in response to both of the first and second Doppler energy values.

78. The method of claim 77 wherein step (c) comprises:
   applying the algorithm to both the first and second Doppler velocity values.

79. The method of claim 75 wherein step (c) comprises:
   bypassing the algorithm where the at least one of the first and second Doppler energy values is less than a threshold.

* * * * *

UNITED STATES PATENT AND TRADEMARK OFFICE
CERTIFICATE OF CORRECTION

PATENT NO.    : 6,179,781 B1
DATED         : January 30, 2001
INVENTOR(S)   : Patrick J. Phillips It is certified that error appears in the above-identified patent and that said Letters Patent is hereby corrected as shown below:

Column 1,
Line 45, delete "detect able" and substitute -- detectable -- in its place.

Column 3,
Line 1, delete "thereof An" and substitute -- thereof. An -- in its place.

Column 8,
Line 35, delete "a, may" and substitute -- α, may -- in its place.

Column 12,
Line 56, delete "09,282,603," and substitute -- 09/282,603, -- in its place.

Column 13,
Line 9, delete "30" and substitute -- + -- in its place.
Line 14, delete "/f$_j$" and substitute -- / (f$_j$ -- in its place (both occurrences).
Line 16, delete "/f$_j$" and substitute -- / (f$_j$ -- in its place (both occurrences).

Signed and Sealed this

Tenth Day of December, 2002

JAMES E. ROGAN
*Director of the United States Patent and Trademark Office*